United States Patent
Yotoriyama et al.

(10) Patent No.: US 9,909,164 B2
(45) Date of Patent: Mar. 6, 2018

(54) METHOD FOR PREPARING SAMPLE FOR NUCLEIC ACID AMPLIFICATION REACTION AND PREPARATION DEVICE OF SAMPLE FOR NUCLEIC ACID AMPLIFICATION REACTION

(71) Applicant: Sony Corporation, Tokyo (JP)

(72) Inventors: Tasuku Yotoriyama, Tokyo (JP); Kazumine Ito, Tokyo (JP); Naohisa Sakamoto, Tokyo (JP); Tomohiko Nakamura, Tokyo (JP)

(73) Assignee: SONY CORPORATION, Tokyo (JP)

( * ) Notice: Subject to any disclaimer, the term of this patent is extended or adjusted under 35 U.S.C. 154(b) by 37 days.

(21) Appl. No.: 14/414,613

(22) PCT Filed: Jun. 10, 2013

(86) PCT No.: PCT/JP2013/065966
§ 371 (c)(1),
(2) Date: Jan. 13, 2015

(87) PCT Pub. No.: WO2014/017187
PCT Pub. Date: Jan. 30, 2014

(65) Prior Publication Data
US 2015/0203894 A1   Jul. 23, 2015

(30) Foreign Application Priority Data
Jul. 25, 2012   (JP) .................. 2012-165130

(51) Int. Cl.
C12Q 1/68    (2006.01)
G01N 27/447  (2006.01)
G01N 1/40    (2006.01)

(52) U.S. Cl.
CPC ......... *C12Q 1/6806* (2013.01); *G01N 27/447* (2013.01); *G01N 2001/4038* (2013.01)

(58) Field of Classification Search
CPC .......... C12Q 1/6806; G01N 1/34; G01N 1/44; G01N 2001/4016; G01N 2001/4038; G01N 2001/38; G01N 2001/381; B01D 61/42
See application file for complete search history.

(56) References Cited

U.S. PATENT DOCUMENTS 6,284,117 B1 * 9/2001 Smolko ............... B01D 61/002
                                                            204/543
2005/0095626 A1   5/2005 Komazawa et al.
(Continued)

FOREIGN PATENT DOCUMENTS

| DE | 19801730 A1 * | 7/1999 | ............ C12M 47/06 |
| JP | 2008-048736 | 3/2003 | |
| JP | 2005-095003 | 4/2005 | |
| JP | 2006-337363 | 12/2006 | |
| JP | 2007-325568 | 12/2007 | |

OTHER PUBLICATIONS

P. Gascoyne, J. Satayavivad, M. Ruchirawat. "Microfluidic approaches to malaria detection" Acta Tropica. Feb. 2004. vol. 89, Issue 3. pp. 357-369.*

(Continued)

*Primary Examiner* — Steven A. Friday
(74) *Attorney, Agent, or Firm* — Chip Law Group (57) ABSTRACT

There is provided a method for preparing a sample for a nucleic acid amplification reaction, the method including a heating step of applying heat to a nucleic acid-containing sample, and an electrodialysis step of bringing an electrical conductivity of the sample to 2,000 µS/cm or less.

14 Claims, 7 Drawing Sheets

(56) References Cited

U.S. PATENT DOCUMENTS

| | | | |
|---|---|---|---|
| 2005/0142565 A1* | 6/2005 | Samper | B01L 3/5027 435/6.11 |
| 2006/0266650 A1* | 11/2006 | Han | B01D 61/422 204/518 |
| 2007/0281307 A1 | 12/2007 | Lee et al. | |
| 2008/0017513 A1* | 1/2008 | Bazinet | B01D 61/425 204/530 |
| 2008/0020380 A1* | 1/2008 | Patno | B01L 7/52 435/6.12 |
| 2008/0044880 A1 | 2/2008 | Han et al. | |
| 2009/0263870 A1* | 10/2009 | Pipper | C12P 19/34 435/91.2 |
| 2010/0297710 A1* | 11/2010 | Hoyal-Wrightson | C12N 15/1003 435/91.52 |
| 2011/0236960 A1* | 9/2011 | Bird | B01F 11/0071 435/283.1 |

OTHER PUBLICATIONS

E.M. Fykse, J.S. Olsen, G. Skogan. "Application of sonication to release DNA from Bacillus cereus for quantitative detection by real-time PCR" Journal of Microbiological Methods. Oct. 2003. vol. 55, Issue 1. pp. 1-10.*

W. Trager and J.B. Jensen. "Human malaria parasites in continuous culture" Science. Aug. 20, 1976. vol. 193, Issue 4254. pp. 673-675.*

F. Palmieri, N. Petrosillo, M.G. Paglia, A. Conte, D. Goletti, L.P. Pucillo, M. Menegon, A.Sannella, C. Severini, G. Majori. "Genetic Confirmation of Quinine-Resistant Plasmodium falciparum Malaria Followed by Postmalaria Neurological Syndrome in a Traveler from Mozambique" Journal of Clinical Microbiology. Nov. 2004 vol. 42, Issue 11. pp. 5424-5426.*

Issadore, D.A. "Hybrid Integrated Circuit/Microfluidic Chips for the Control of Living Cells and Ultra—Small Biomimetic Containers" Dissertation. Harvard University. May 2009 (Year: 2009).*

Lewpiriyawong, N. and Yang, C. "Dielectrophoresis Field-Flow Fractionation for Continuous-Flow Separation of Particles and Cells in Microfluidic Devices" Advances in Transport Phenomena 2011. vol. 3. no date 2014 (Year: 2014).*

Voldman, J. "Electrical Forces for Microscale Cell Manipulation" Annual Review of Biomedical Engineering. Mar. 29, 2006 (Year: 2006).*

Rodriguez-Mejia JL., et al., "A two-step electrodialysis method for DNA purification from polluted metallic environmental samples," Electrophoresis, 2008, vol. 29, No. 15, p. 3239-3244.

* cited by examiner

METHOD FOR PREPARING SAMPLE FOR NUCLEIC ACID AMPLIFICATION REACTION AND PREPARATION DEVICE OF SAMPLE FOR NUCLEIC ACID AMPLIFICATION REACTION

CROSS REFERENCES TO RELATED APPLICATIONS

The present application is a national stage of International Application No. PCT/JP2013/065966 filed on Jun. 10, 2013 and claims priority to Japanese Patent Application No. 2012-165130 filed on Jul. 25, 2012, the disclosure of which is incorporated herein by reference.

BACKGROUND

The present technology relates to a method for preparing a sample for a nucleic acid amplification reaction, and a preparation device of a sample for a nucleic acid amplification reaction. More specifically, the present technology relates to a method and the like that includes a step of heating a sample and an electrodialysis step.

A method for analyzing the nucleic acids contained in a sample is utilized, for example in the medical field, for nucleic acid testing and the like for diagnosis of infectious diseases. In such nucleic acid testing, the nucleic acids in the sample are usually subjected to a nucleic acid amplification reaction in advance, and the target nucleic acid is amplified to the required level for testing. Especially, when the nucleic acid to be tested for is contained in a low concentration in the sample, the nucleic acid amplification reaction is an essential step in nucleic acid analysis.

In many cases a nucleic acid-containing sample contains substances that inhibit the nucleic acid amplification reaction. Consequently, in order to amplify the nucleic acids in the sample, the nucleic acids are usually purified by removing the substances other than nucleic acids from the sample. For example, Patent Literature 1 describes a method for isolating nucleic acids by causing the nucleic acids in a sample to be adsorbed to a nucleic-acid-absorbent porous membrane.

This method includes a step of passing a sample solution containing nucleic acids through a nucleic-acid-absorbent porous membrane to cause the nucleic acids to be adsorbed in the nucleic-acid-absorbent porous membrane, a step of washing the nucleic-acid-absorbent porous membrane with the nucleic acids adsorbed to the membrane by passing a washing solution through the nucleic-acid-absorbent porous membrane, and a step of desorbing the nucleic acids from the nucleic-acid-absorbent porous membrane by passing a recovery solution through the nucleic-acid-absorbent porous membrane.

Further, a method has been disclosed for reducing the effects of substances that inhibit a nucleic acid amplification reaction by adding a separate reagent to the components that inhibit the nucleic acid amplification reaction which remain in the nucleic acid-containing sample, or in a recovery solution and the like containing the nucleic acids recovered by a purification method like that described above.

For example, in the nucleic acid analysis method disclosed in Patent Literature 2, a step is included for treating a nucleic acid purification solution with an enzyme that acts on the amplification inhibition substances in the sample or in the nucleic acid purification reagent to convert them into substances that do not inhibit amplification as much.

CITATION LIST

Patent Literature

Patent Literature 1: JP 2005-95003A
Patent Literature 2: JP 2007-325568A

SUMMARY

Technical Problem

Based on the separation and purification method of nucleic acids described in Patent Literature 1, the nucleic acids can be purified to a level that is suitable for a nucleic acid amplification reaction. However, in a nucleic acid purification method that utilizes a nucleic-acid-absorbent porous membrane, in each of the adsorbing, washing, and recovery steps, the solution used in each step has to pass through the nucleic-acid-absorbent porous membrane, so the purification operation is complicated.

On the other hand, in the nucleic acid analysis method described in Patent Literature 2, the effects of inhibitory substances on a nucleic acid amplification reaction are reduced by adding an enzyme solution that contains an alcohol degrading enzyme and the like to the nucleic acid-containing sample. However, it is usually preferred that the enzyme solution is prepared beforehand. Since an operation for mixing the components contained in the enzyme solution, such as the enzyme and the buffer solution, to predetermined concentrations has to be carried out each time a sample for a nucleic acid amplification reaction is to be prepared, the operation for preparing the sample for the nucleic acid amplification reaction is complicated. Therefore, a main object of the present technology is to provide a method for preparing a nucleic acid-containing sample in a state suitable for a nucleic acid amplification reaction simply and that does not involve complicated steps.

Solution to Problem

So as to solve the problem, according to the present disclosure, there is provided a method for preparing a sample for a nucleic acid amplification reaction, the method including a heating step of applying heat to a nucleic acid-containing sample, and an electrodialysis step of bringing an electrical conductivity of the sample to 2,000 μS/cm or less.

A porous membrane used in the electrodialysis step preferably has an average pore size of 100 nm or less. A heating temperature of the sample in the heating step is preferably 50° C. or more to 65° C. or less.

The method for preparing a sample for a nucleic acid amplification reaction may further includes a step of performing an ultrasonic treatment on the sample. The method for preparing a sample for a nucleic acid amplification reaction may further includes a step of diluting the sample.

The sample may include a sample derived from a living organism. The sample derived from a living organism may be plasma, serum, or cerebrospinal fluid.

When the sample derived from a living organism is cerebrospinal fluid, the method for preparing a sample for a nucleic acid amplification reaction may include the heating step, and the electrodialysis step after the heating step.

When the nucleic acid is a nucleic acid that is present in a cell included in the sample derived from a living organism, the method for preparing a sample for a nucleic acid amplification reaction may include the heating step, the electrodialysis step after the heating step, and the step of performing an ultrasonic treatment on the sample after the electrodialysis step.

When the sample derived from a living organism is plasma or serum, the method for preparing a sample for a nucleic acid amplification reaction includes the electrodialysis step, the heating step after the electrodialysis step, and the step of diluting the sample after the heating step.

The nucleic acid amplification reaction may be an isothermal nucleic acid amplification reaction.

The isothermal nucleic acid amplification reaction may be performed based on a loop-mediated isothermal amplification method.

In addition, according to the present disclosure, there is provided a preparation device of a sample for a nucleic acid amplification reaction, the preparation device including a first space that contains a sample, a second space in which an anode is arranged, and a third space in which a cathode is arranged. A boundary between the second space and the first space and a boundary between the third space and the first space are each separated by a porous membrane. The preparation device further includes a power source configured to apply a voltage to the anode and the cathode, and a heating unit configured to apply heat to the first space.

The preparation device of a sample for a nucleic acid amplification reaction may further includes an ultrasonic wave generation unit configured to generate a ultrasonic wave. A part of a surface constituting the first space may be formed in a manner that ultrasonic wave can be transmitted to the sample.

In addition, according to the present disclosure, there is provided a preparation vessel of a sample for a nucleic acid amplification reaction, the preparation vessel including a first space that contains a sample, a second space in which an anode is arranged, and a third space in which a cathode is arranged. A boundary between the second space and the first space and a boundary between the third space and the first space are each separated by a porous membrane.

Advantageous Effects of Invention

According to the present technology, provided is a method for preparing a nucleic acid-containing sample as a sample for a nucleic acid amplification reaction based on a simple operation.

Additional features and advantages are described herein, and will be apparent from the following Detailed Description and the figures.

DETAILED DESCRIPTION

Figure 1:
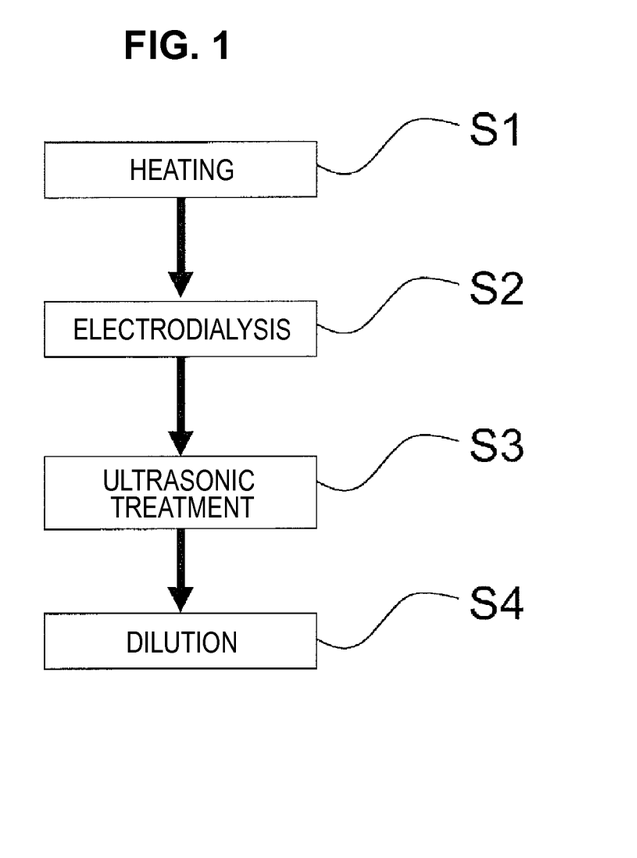
FIG. 1 is a flowchart illustrating a method for preparing a sample for a nucleic acid amplification reaction according to the present technology.

Hereinafter, preferred embodiments of the present invention will be described in detail with reference to the appended drawings. Note that, in this specification and the drawings, elements that have substantially the same function and structure are denoted with the same reference signs, and repeated explanation is omitted. The description will be carried out in the following order.
1. Method for Preparing the Sample for a Nucleic Acid Amplification Reaction According to the Present Technology
(1) Sample and Nucleic Acid Amplification Reaction
(2) Preparation Method
(2-1) Heating Step
(2-2) Electrodialysis Step
(2-3) Ultrasonic Treatment Step
(2-4) Dilution Step
2. Specific Examples of the Method for Preparing the Sample for a Nucleic Acid Amplification Reaction According to the Present Technology
(1) Cerebrospinal Fluid
(2) Cell-Containing Sample
(3) Plasma
3. Preparation Vessel of the Sample for a Nucleic Acid Amplification Reaction According to the Present Technology
(1) Preparation Vessel Configuration
(2) Preparation of a Sample for a Nucleic Acid Amplification Reaction Using the Preparation Vessel
1. Method for Preparing the Sample for a Nucleic Acid Amplification Reaction According to the Present Technology FIG. 1 is a flowchart illustrating a method for preparing a sample for a nucleic acid amplification reaction according to the present technology. The method for preparing a sample for a nucleic acid amplification reaction (hereinafter, simply referred to as "sample preparation method") includes a heating step S1, an electrodialysis step S2, an ultrasonic treatment step S3, and a dilution step S4, which are each shown in the flowchart.

(1) Sample and Nucleic Acid Amplification Reaction

Before describing each of the steps illustrated in FIG. 1, first, the sample and the nucleic acid amplification reaction that are the object of the method for preparing a sample for a nucleic acid amplification reaction according to the present technology will be described.

In the sample preparation method according to the present technology, the term "sample" is not especially limited, and may refer to, for example, an animal-derived, a plant-derived, a fungus-derived, a bacteria-derived, or a virus-derived sample that includes the nucleic acid to be amplified in the nucleic acid amplification reaction. The nucleic acid may be either a single strand or a double strand, and may be either DNA or RNA. Further, the molecular weight of the nucleic acid is also not especially limited. It is noted that the nucleic acid contained in the sample may be, like a bacterial genome present in the cells of a bacteria, in a state in which it is not directly dispersed in the sample, but rather is surrounded by a membrane such as a cellular membrane, or is present inside particles.

Examples of the nucleic acid-containing sample include samples containing a sample derived from a living organism. Examples of samples derived from a living organism include bodily fluids such as whole blood, plasma, serum, cerebrospinal fluid, urine, semen, saliva and the like. A "sample" containing a sample derived from a living organism may include a component to be added to the sample derived from a living organism during collection, such as an anticoagulant like heparin and EDTA, for example. It is especially preferred that the method for preparing a sample for a nucleic acid amplification reaction according to the present technology is used to prepare plasma, serum, or cerebrospinal fluid.

Examples of the "nucleic acid amplification reaction" that is the object of the sample preparation method according to the present technology may include a conventional PCR (polymerase chain reaction) method that employs thermal cycling, as well as various isothermal amplification methods that do not involve thermal cycling. Examples of isothermal amplification methods include methods such as LAMP (loop-mediated isothermal amplification), and TRC (transcription-reverse transcription concerted). As the method for preparing a sample for a nucleic acid amplification reaction according to the present technology, an isothermal amplification method is preferred. As such an isothermal amplification method, a LAMP method, for example, is preferred.

(2) Preparation Method

Next, the sample preparation method according to the present technology will be described in order with reference to the flowchart (FIG. 1). It is noted that although the heating step S1 and the electrodialysis step S2 are essential steps in the sample preparation method according to the present technology, the ultrasonic treatment step S3 and the dilution step S4 are not essential steps. The ultrasonic treatment step S3 and the dilution step S4 are steps that may be appropriately added based on the selected sample. Further, the respective order of the heating step S1, the electrodialysis step S2, and the dilution step S4 is not limited to the order of the flowchart illustrated in FIG. 1, these steps may be carried out in any order.

As described below, if a nucleic acid present in a cell such a bacteria is the amplification target, for example, it is preferred to add the ultrasonic treatment step S3 to the sample preparation method according to the present technology. Since a nucleic acid is less susceptible to the effects of heating of the sample and to changes in salt concentration when the nucleic acid is held inside cells in the sample, it is preferred to perform the ultrasonic treatment step S3 after the heating step S1 and the electrodialysis step S2.

(2-1) Heating Step

In FIG. 1, reference symbol S1 indicates a step of heating a nucleic acid-containing sample. In this step, the nucleic acid-containing sample is heated to reduce the effects on the nucleic acid amplification reaction of substances that inhibit the nucleic acid amplification reaction. It is preferred that the heating temperature in the heating step S1 is 50° C. or more to 65° C. or less. If the heating temperature of the sample is too low, the reduction in the effects of substances that inhibit the nucleic acid amplification reaction are insufficient. Consequently, when the sample is used in the nucleic acid amplification reaction, the nucleic acid in the sample is not amplified. On the other hand, if the heating temperature of the sample is too high, the proteins and the like included in the sample are denatured, turning the sample into a gel. Consequently, it is difficult to use the heated sample in the nucleic acid amplification reaction.

At 60° C., it is preferred that the heating time of the sample is 10 minutes or more. Further, after performing the heating step S1, it is preferred to cool the sample once before using the sample in the nucleic acid amplification reaction. Examples of the cooling method include, but are not especially limited to, "rapid cooling", in which the sample is actively cooled by placing on ice and the like, and "gradual cooling", in which the sample is gradually cooled by leaving the sample to stand at room temperature.

(2-2) Electrodialysis Step

In FIG. 1, reference symbol S2 indicates an electrodialysis step carried out so that the nucleic acid-containing sample has an electrical conductivity of 2,000 μS/cm or less. In this step, the electrical conductivity of the sample is reduced by removing from the sample a part of the molecules included the sample that have an electric charge by electrodialysis. In electrodialysis, since dialysis can be carried out while monitoring electrical conductivity, it is simple to perform the dialysis operation so that a desired electrical conductivity is reached. In the sample preparation method according to the present technology, it is preferred the electrical conductivity of the sample by performing the electrodialysis step S2 is 2,000 μS/cm or less, and more preferably 1,000 μS/cm or less. The electrodialysis conditions are not especially limited. The operator may appropriately select the current value and the voltage value based on the properties and the like of each sample.

The porous membrane used in the electrodialysis step is provided with holes having a size that, among the charged particles included in the sample, allows the molecules that are targeted for separation from the sample, such as salts, to pass through, and keep molecules, such as nucleic acids, in the sample without passing out. Consequently, mainly salts are removed from the sample by the electrodialysis step S2, which enables desalting of the sample.

Although the average pore size of the porous membrane may be selected based on the composition of the selected sample, the type of nucleic acid and the like, it is preferred that the average pore size is, for example, 100 nm or less. Further, the material of the porous membrane can be selected from among materials known as dialysis membranes, such as cellulose acetate, regenerated cellulose, and polycarbonate. In addition, an ion-exchange membrane can also be used as the porous membrane.

(2-3) Ultrasonic Treatment Step

In FIG. 1, reference symbol S3 indicates a step of performing an ultrasonic treatment on the sample (FIG. 1, ultrasonic treatment step S3). If a nucleic acid present in a cell that is included in the sample is the target of the nucleic acid amplification reaction, in the sample preparation method according to the present technology, it is preferred, but not essential, to include this step in the sample preparation method. By carrying out the ultrasonic treatment step S3, the cell membranes of the cells included in the sample are broken down by ultrasonic waves. This makes it easier for the nucleic acids to be released into the sample from inside the cells, so that the efficiency of the nucleic acid amplification reaction increases.

The ultrasonic treatment step S3 can be carried out utilizing a known ultrasonic wave generation device. For the irradiation of the ultrasonic waves on the sample, a contact-type ultrasonic wave generation device, like a horn immersion type ultrasonic wave generation device, may be used. Alternatively, ultrasonic waves may be transmitted to the sample via the vessel or the like, with a non-contact type ultrasonic wave generation device. The frequency of the ultrasonic waves can be appropriately selected in a range of kHz to MHz based on the performance of the ultrasonic wave generation device and the properties of the sample.

(2-4) Dilution Step S4

In FIG. 1, reference symbol S4 indicates a step of diluting the nucleic acid-containing sample (FIG. 1, dilution step S4). Similar to the ultrasonic treatment step S3, for a sample that has a high protein concentration, such as a sample of plasma, serum and the like, for example, in the sample preparation method according to the present technology, it is preferred, but not essential, to add this step in the sample preparation method. By carrying out the dilution step S4, the concentration of substances included in the sample that inhibit the nucleic acid amplification reaction is reduced, so that the efficiency of the nucleic acid amplification reaction increases.

Examples of the solvent used for the dilution are not especially limited, and may include sterilized water, normal saline solution and the like. For example, normal saline solution may be used to dilute the sample before performing the electrodialysis step S2, and sterilized water may be used to dilute the sample after the electrodialysis step S2. In the dilution step S4, it is preferred to add the sterilized water and normal saline solution to the sample so that the ultimate sample for a nucleic acid amplification reaction to which enzymes, primers and the like have been added that is prepared for the nucleic acid amplification reaction is diluted by a factor of about 2 to 10 of the sample before preparation.

As described above, the method for preparing a sample for a nucleic acid amplification reaction according to the present technology includes the heating step S1, the electrodialysis step S2, the ultrasonic treatment step S3, and the dilution step S4. Among the aspects of the method for preparing a sample for a nucleic acid amplification reaction according to the present technology, when using the sample in the nucleic acid amplification reaction by performing only the heating step S1 and the electrodialysis step S2, while each step is being carried out, the sample is maintained in a state in which it is contained in the vessel that is used in each step. As a result, complicated operations such as adding a reagent solution by opening and closing the vessel, and removing waste liquid from the vessel, are not performed. Consequently, the preparation of the sample for a nucleic acid amplification reaction can be simply carried out.

Further, by including the ultrasonic treatment step S3 and the dilution step S4 in the method for preparing a sample for a nucleic acid amplification reaction according to the present technology, the nucleic acid amplification reaction using the sample can be carried out without performing complicated operations even when the nucleic acid to be amplified is present in a cell or when the sample contains a high concentration of proteins.

In addition, the method for preparing a sample for a nucleic acid amplification reaction according to the present technology does not use a reagent that is prepared beforehand, such as the enzyme solution described in Patent Literature 2. Consequently, the preparation for preparing the sample for a nucleic acid amplification reaction is simple, so that the sample for a nucleic acid amplification reaction can be prepared in a shorter period of time.

2. Specific Examples of the Method for Preparing the Sample for a Nucleic Acid Amplification Reaction According to the Present Technology The above-described method for preparing a sample for a nucleic acid amplification reaction according to the present technology will is described below based on the examples of cerebrospinal fluid sample, a cell-containing sample, and a plasma sample, respectively.

(1) Cerebrospinal Fluid

When the sample is cerebrospinal fluid, and a virus contained in this cerebrospinal fluid is the target of the nucleic acid amplification reaction, the sample can be used in the nucleic acid amplification reaction by performing the heating step S1, and then performing the electrodialysis step S2 after the heating step S1, of the above-described method for preparing a sample for a nucleic acid amplification reaction according to the present technology.

(2) Cell-Containing Sample

Unlike the above-described virus-containing sample and the like, when the nucleic acid to be amplified is a nucleic acid that is present in a cell contained in a sample derived from a living organism, such as a bacterial genome, since the nucleic acid present in the sample is surrounded by a cell membrane, if only the above-described heating step S1 and electrodialysis step S2 are carried out, the nucleic acid will stay in the cell, and not be easily released into the sample. Accordingly, for such a sample, after the heating step S1 and the electrodialysis step S2 performed after the heating step S1 of the above-described method for preparing a sample for a nucleic acid amplification reaction according to the present technology, the ultrasonic treatment step S3 is also included to increase the ratio of nucleic acid that is released into the sample. Consequently, the efficiency of the nucleic acid amplification reaction can be increased.

(3) Plasma

Compared with cerebrospinal fluid, plasma has a high protein concentration. Consequently, plasma has a high content of components that inhibit the nucleic acid amplification reaction, so that for a sample on which only the above-described heating step S1 and electrodialysis step S2 have been performed, the reduction in the effects of substances inhibiting the nucleic acid amplification reaction is not sufficient. Accordingly, for such a sample, after the heating step S1 and the electrodialysis step S2 performed after the heating step S1 of the above-described method for preparing a sample for a nucleic acid amplification reaction according to the present technology, the dilution step S4 is also included to reduce the concentration of inhibitory substances in the sample. Consequently, the efficiency of the nucleic acid amplification reaction can be increased.

Figure 2:
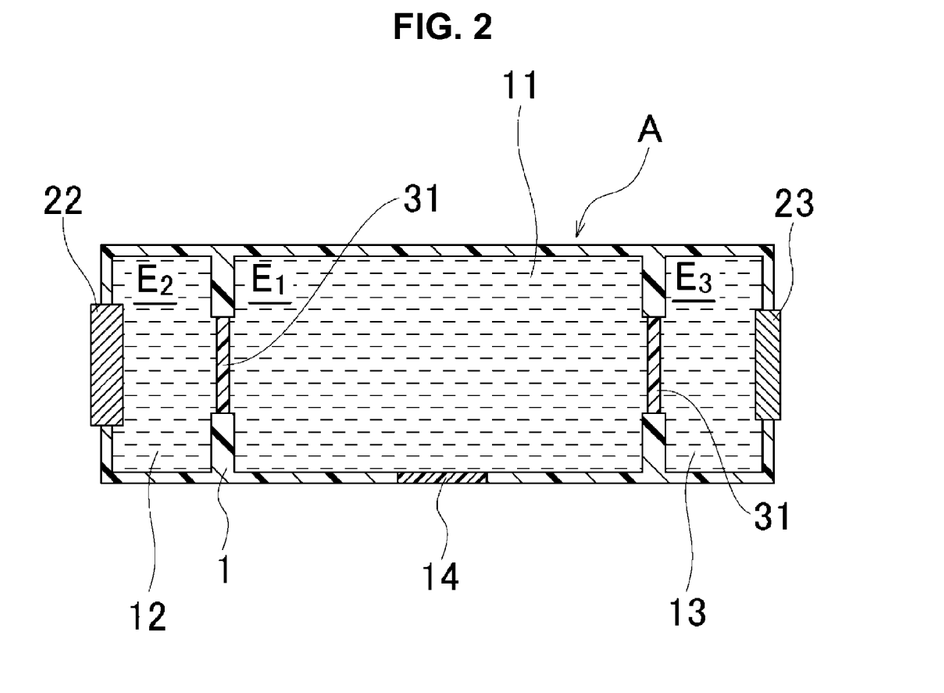
FIG. 2 is a cross-sectional schematic view of a preparation vessel that is included in a preparation device of a sample for a nucleic acid amplification reaction according to the present technology.

3. Preparation Vessel of the Sample for a Nucleic Acid Amplification Reaction According to the Present Technology FIG. 2 is a cross-sectional schematic view of a preparation vessel of a sample for a nucleic acid amplification reaction according to the present technology. The preparation vessel is now described with reference to FIG. 2.

(1) Preparation Vessel Configuration

The preparation vessel represented by the reference symbol A in FIG. 2 includes a body 1 and electrodes (an anode 22 and a cathode 23). The body 1 has three spaces, a first space $E_1$, a second space $E_2$, and a third space $E_3$. In FIG. 2 and the description thereof, $E_1$ refers to a sample containing-section 11 (first space) that contains the sample, $E_2$ refers to an electrolyte-containing section 12 (second space) in which the anode 22 is formed and that contains an electrolyte, and $E_3$ refers to an electrolyte-containing section 13 (third space) in which the cathode 23 is formed and that contains an electrolyte, respectively. At the boundary between the sample containing-section 11 and the electrolyte-containing section 12, and at the boundary between the sample containing-section 11 and the electrolyte-containing section 13, respectively, a porous membrane 31 is provided, whereby each of the spaces $E_1$, $E_2$, and $E_3$ are separated.

The material of the body 1 is not especially limited, as long as the material has an insulating property, and is resistant to the heating and the irradiation of ultrasonic waves that the vessel is subjected to in the above-described sample preparation method. Known thermoplastic resins may be used, such as, for example, polyethylene, polystyrene, polypropylene, acrylic resin, cyclic polyolefin and the like.

Further, a part of the surface constituting the sample containing-section 11 of the body 1 is formed so that ultrasonic waves can be transmitted to the sample. For example, like the preparation vessel A illustrated in FIG. 2, an ultrasonic wave transmission portion 14 may be provided. The ultrasonic wave transmission portion 14, for example, is configured from a material such as hard plastic or metal so that when ultrasonic waves generated by the ultrasonic wave generation device are irradiated on the ultrasonic wave transmission portion 14, vibrations can be transmitted via the ultrasonic wave transmission portion 14 to the sample in the space $E_1$.

Further, by forming the ultrasonic wave transmission portion 14 from an elastic material, such as an elastomer like a silicone elastomer or an acrylic elastomer, or natural rubber, ultrasonic waves can also be directly irradiated on the sample in the space $E_1$ by puncturing the ultrasonic wave transmission portion 14 with a part of a vibration transmission piece of the ultrasonic wave generation device. The material of the ultrasonic wave transmission portion 14 is not especially limited, as long as the ultrasonic wave transmission portion 14 is formed so that ultrasonic waves can be transmitted to the sample in the sample containing-section 11. In addition, the position where the ultrasonic wave transmission portion 14 is provided is not limited to the position illustrated in FIG. 2.

The porous membranes 31 and 31 separating the electrolyte-containing sections 12 and 13 from the sample containing-section 11 may be appropriately selected from porous membranes formed from the materials described above based on the characteristics and the like of the sample. It is noted that the porous membrane 31 provided at the boundary between the space $E_1$ and space $E_3$ and the porous membrane 31 provided at the boundary between the space $E_1$ and space $E_3$ may be different. The membrane 31 provided at each boundary may be formed from different materials and have different properties.

Known materials that are used for electrodes may be used for the material of the respective electrodes, the anode 22 and the cathode 23. Examples of such materials include metals such as gold, platinum, iridium oxide, and titanium nitride.

Figure 3:
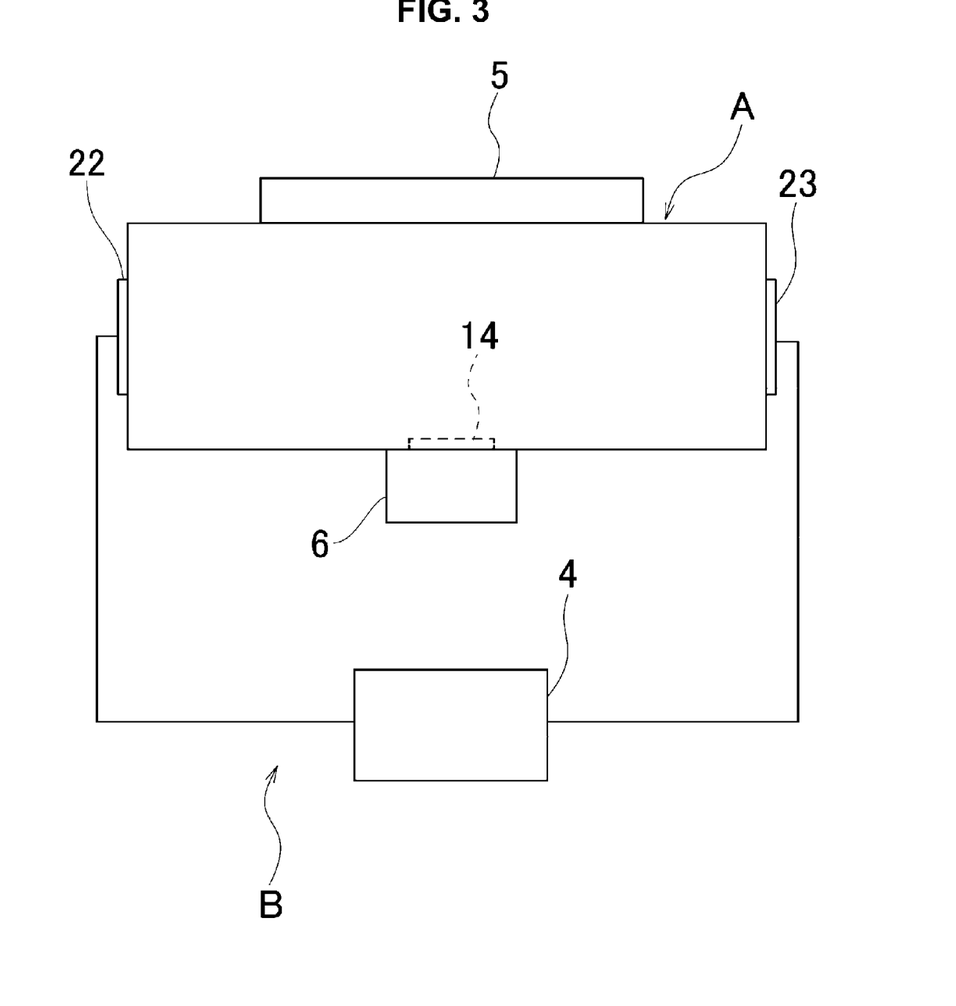
FIG. 3 is a schematic view of a preparation device of a sample for a nucleic acid amplification reaction according to the present technology.

Further, as illustrated in FIG. 3, a preparation device B of the sample for a nucleic acid amplification reaction can also be configured by including in the above-described preparation vessel A a power supply 4 that applies a voltage to the anode 22 and the cathode 23, and a heating unit 5 that applies heat to the sample containing-section 11 (first space). In addition, the preparation device B of the sample for a nucleic acid amplification reaction may also include an ultrasonic wave generation unit 6 for generating ultrasonic waves.

(2) Preparation of a Sample for a Nucleic Acid Amplification Reaction Using the Preparation Vessel Next, the method for preparing a sample for a nucleic acid amplification reaction that uses the preparation vessel A illustrated in FIG. 2 will be described.

First, the nucleic acid-containing sample is introduced into the sample containing-section 11 of the preparation vessel A, and an electrolyte is introduced into the electrolyte-containing sections 12 and 13. The type of electrolyte that is introduced into the preparation vessel A is not especially limited, and may be appropriately selected based on the properties of the sample and the electrodialysis conditions. For example, the electrolyte may include calcium hydroxide, sodium hydroxide, potassium chloride, sodium chloride and the like.

In the method for preparing a sample for a nucleic acid amplification reaction that uses the preparation vessel A, when subjected to the above-described heating step S1, the electrodialysis step S2, and the ultrasonic treatment step S3, the sample contained in the preparation vessel A is in a state in which it is contained in the preparation vessel A. It is noted that the dilution step S4 may be carried out by adding an appropriate liquid before the sample is introduced into the preparation vessel A, or after each step has been completed and the sample collected from the preparation vessel A.

In the preparation of the sample carried out using the preparation vessel A, although the order of the heating step S1 and the electrodialysis step S2 is not especially limited, here this order will be described in the order illustrated in the flowchart of FIG. 1. Further, the ultrasonic treatment step S3 and the dilution step S4 are not essential steps in the preparation of the sample carried out using the preparation vessel A, that can be added based on the properties of the sample and the like.

In the heating step S1 of the sample, the sample is heated by placing the preparation vessel A on a heating device, such as a heat block or in a thermostatic bath, to heat the sample containing-section 11. The preferred heating time and heating temperature the heating step S1 are as described above. After the heating step S1 has been completed, the preparation vessel A is cooled by rapid cooling or gradual cooling.

After the preparation vessel A has been subjected to the heating step S1, in the electrodialysis step S2, a voltage is applied to the anode 22 and the cathode 23 to subject the sample to electrodialysis. By applying a voltage to the electrodes, the charged substances included in the sample move toward the anode 22 or the cathode 23 based on their charge. Since porous membranes 31 and 31 are provided between the sample containing-section 11 and the electrolyte-containing sections 12 and 13, molecules that are larger than the diameter of the holes present in the porous membranes 31 and 31 cannot pass through the porous membranes, but molecules that are smaller than the diameter of the pores can pass through. Consequently, mainly lowmolecular-weight molecules, such as salts, move out of the sample containing-section 11 by the electrodialysis, and high-molecular-weight molecules, such as genomes, stay in the sample containing-section 11, whereby the sample is desalted.

In the electrodialysis step S2, a sample whose electrical conductivity has reached 2,000 μS/cm or less is then subjected to an ultrasonic treatment in the ultrasonic treatment step S3. The ultrasonic treatment on the sample contained in the sample containing-section 11 can be, as described above, performed via the ultrasonic wave transmission portion 14. The preferred frequency and irradiation time of the ultrasonic waves in the ultrasonic treatment step S3 are as described above.

As described above, by preparing the sample for a nucleic acid amplification reaction using the preparation vessel A according to the present technology, especially when the sample is prepared only by the heating step S1 and the electrodialysis step S2, a sample that is suitable to a nucleic acid amplification reaction can be simply prepared. Further, when preparing the sample using the preparation vessel A, since the heating step S1, the electrodialysis step S2, and the ultrasonic treatment step S3 can be carried out in a state in which the sample is contained in the preparation vessel A, preventing contamination of the sample is simple. In addition, when the sample contains pathogens, such as bacteria or viruses, there are fewer opportunities for exposure of the operator to the pathogens, so that the sample can be prepared more safely.

Additionally, the present technology may also be configured as below.

(1)
A method for preparing a sample for a nucleic acid amplification reaction, the method including:
a heating step of applying heat to a nucleic acid-containing sample; and
an electrodialysis step of bringing an electrical conductivity of the sample to 2,000 μS/cm or less.

(2)
The method for preparing a sample for a nucleic acid amplification reaction according to (1), wherein a porous membrane used in the electrodialysis step has an average pore size of 100 nm or less.

(3)
The method for preparing a sample for a nucleic acid amplification reaction according to (1) or (2), wherein a heating temperature of the sample in the heating step is 50° C. or more to 65° C. or less.

(4)
The method for preparing a sample for a nucleic acid amplification reaction according to any one of (1) to (3), the method further including:
a step of performing an ultrasonic treatment on the sample.

(5)
The method for preparing a sample for a nucleic acid amplification reaction according to any one of (1) to (4), the method further including:
a step of diluting the sample.

(6)
The method for preparing a sample for a nucleic acid amplification reaction according to any one of (1) to (5), wherein the sample includes a sample derived from a living organism.

(7)
The method for preparing a sample for a nucleic acid amplification reaction according to (6), wherein the sample derived from a living organism is plasma, serum, or cerebrospinal fluid.

(8)
The method for preparing a sample for a nucleic acid amplification reaction according to (7), wherein when the sample derived from a living organism is cerebrospinal fluid, the method includes:
the heating step; and
the electrodialysis step after the heating step.

(9)
The method for preparing a sample for a nucleic acid amplification reaction according to (7), wherein when the nucleic acid is a nucleic acid that is present in a cell included in the sample derived from a living organism, the method includes:
the heating step;
the electrodialysis step after the heating step; and
the step of performing an ultrasonic treatment on the sample after the electrodialysis step.

(10)
The method for preparing a sample for a nucleic acid amplification reaction according to (7), wherein when the sample derived from a living organism is plasma or serum, the method includes:
the electrodialysis step;
the heating step after the electrodialysis step; and
the step of diluting the sample after the heating step.

(11)
The method for preparing a sample for a nucleic acid amplification reaction according to any one of (1) to (10), wherein the nucleic acid amplification reaction is an isothermal nucleic acid amplification reaction.

(12)
The method for preparing a sample for a nucleic acid amplification reaction according to (11), wherein the isothermal nucleic acid amplification reaction is performed based on a loop-mediated isothermal amplification method.

EXAMPLES

Example 1

1. Effects of Dilution on the Substances in the Sample that Inhibit a Nucleic Acid Amplification Reaction The effects on a nucleic acid amplification reaction by diluting the nucleic acid-containing sample were investigated. In the present example, bovine plasma solutions diluted with sterilized water by a factor of 3 to 100 were prepared. Further, bovine plasma that was not diluted was also prepared. A bifidobacteria genome purified in advance with a QIAamp DNA Mini kit (manufactured by Qiagen N.V.) was admixed into each of the diluted plasma solutions and the non-diluted bovine plasma to a concentration of 100 copies/μl.

A LAMP reagent in an equal amount to the sample was admixed into each of the plasma solutions to which the bifidobacteria genome had been added, and a nucleic acid amplification reaction based on the LAMP method was carried out on the resultant mixture as a test sample for a nucleic acid amplification reaction. Since a LAMP reagent had been added to the test sample used in the LAMP reaction in an amount equivalent to the diluted plasma, when the mixture was subjected to the nucleic acid amplification reaction, the plasma component included in each test sample was further diluted (by a factor of 6 to 200) by the dilution (factor of 3 to 100). It is noted that in the below-described Examples 2 to 5 too, in the cases in which an equal amount of a LAMP reagent is added, the ultimate concentration of the analyte in the test sample subjected to the nucleic acid amplification reaction is, similar to this example, further diluted by twice the dilution factor during the preparation process.

Figure 4:
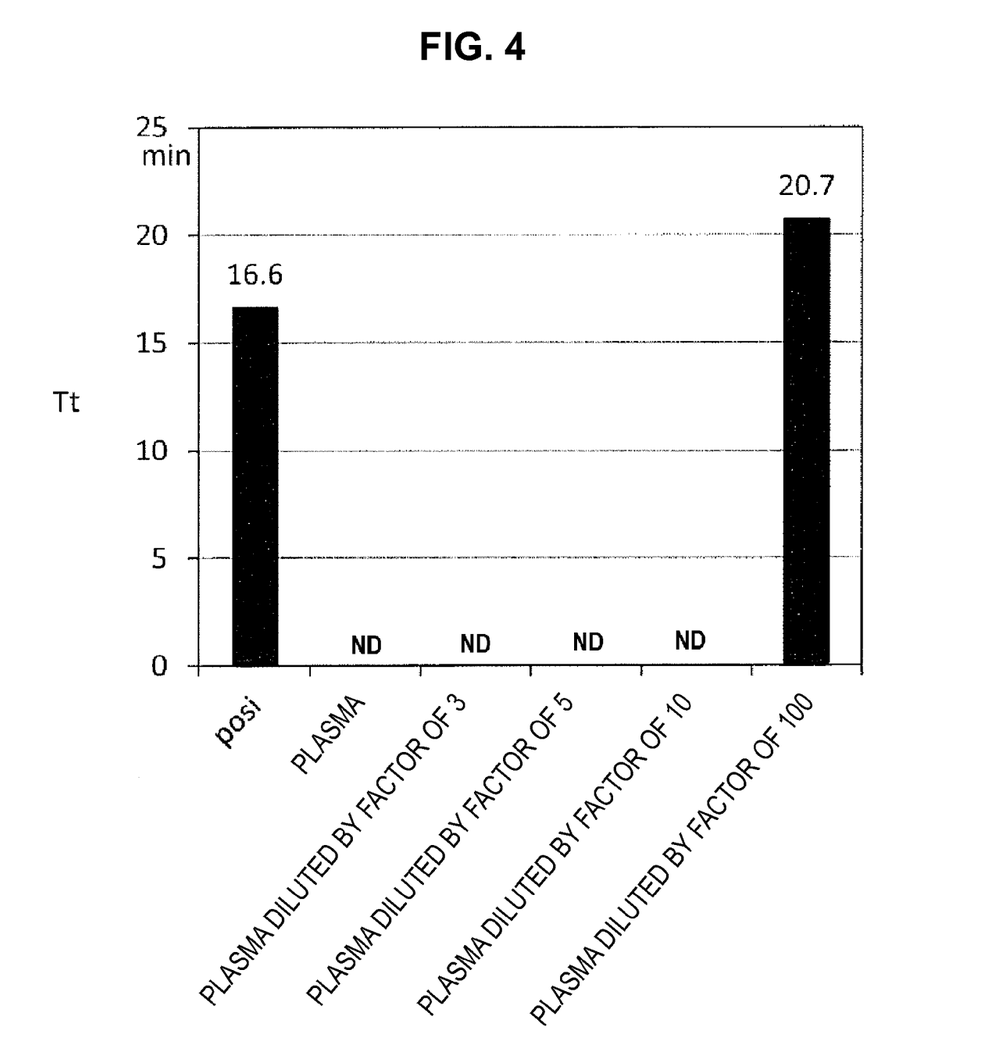
FIG. 4 is a graph illustrating a reduction in the effects of inhibitory substances on a nucleic acid amplification reaction by dilution of a sample (Example 1).

The results of this example are shown in FIG. 4. The vertical axis in FIG. 4 represents a Tt value in the nucleic acid amplification reaction. The Tt value is the time taken from the start of the nucleic acid amplification reaction to the point when the rate of increase in the turbidity of the nucleic acid amplification reaction solution exceeds a predetermined threshold. A smaller Tt value indicates that the nucleic acid amplification reaction is occurring more efficiently.

The column "posi" in FIG. 4 indicates a test sample that does not contain bovine plasma which was prepared with sterilized water so that the concentration of the bifidobacteria genome was 1,000 copies/µl. For the "posi" serving as the positive control of this example, nucleic acid amplification based on the LAMP method was recognized. The Tt value of the "posi" sample was 16.6 minutes.

As illustrated in FIG. 4, for the test samples containing bovine plasma, nucleic acid amplification was not recognized for the non-diluted bovine plasma (FIG. 4, plasma), or for the bovine plasma solutions having a dilution factor of up to 10 (in FIG. 4, ND indicates that an amplified nucleic acid strand was not detected). On the other hand, for the test sample in which bovine plasma was diluted by a factor of 100, nucleic acid amplification was recognized (FIG. 4, plasma diluted by a factor of 100), and the Tt value of this sample was 20.7 minutes. Based on the results of this example, it was confirmed that reducing the components included in the plasma that inhibit a nucleic acid amplification reaction to a predetermined concentration reduces the effects on the nucleic acid amplification reaction.

Example 2

2. Investigation of the Electrical Conductivity of the Sample that Enables a Nucleic Acid Amplification Reaction In this example, the electrical conductivity of the sample that enables a nucleic acid amplification reaction was investigated by focusing on the electrical conductivity of the samples.

In this example, commercially-available normal saline solution (Otsuka Pharmaceutical) was used as a pseudo-analyte. The normal saline solution was diluted with sterilized water so that electrical conductivity was in the range of 7,300 µS/cm to 280 µS/cm. A bifidobacteria genome was added to the diluted normal saline solution to a concentration of 100 copies/µl to prepare a test sample for a nucleic acid amplification reaction. The nucleic acids in the test sample for a nucleic acid amplification reaction were amplified based on the LAMP method.

Figure 5:
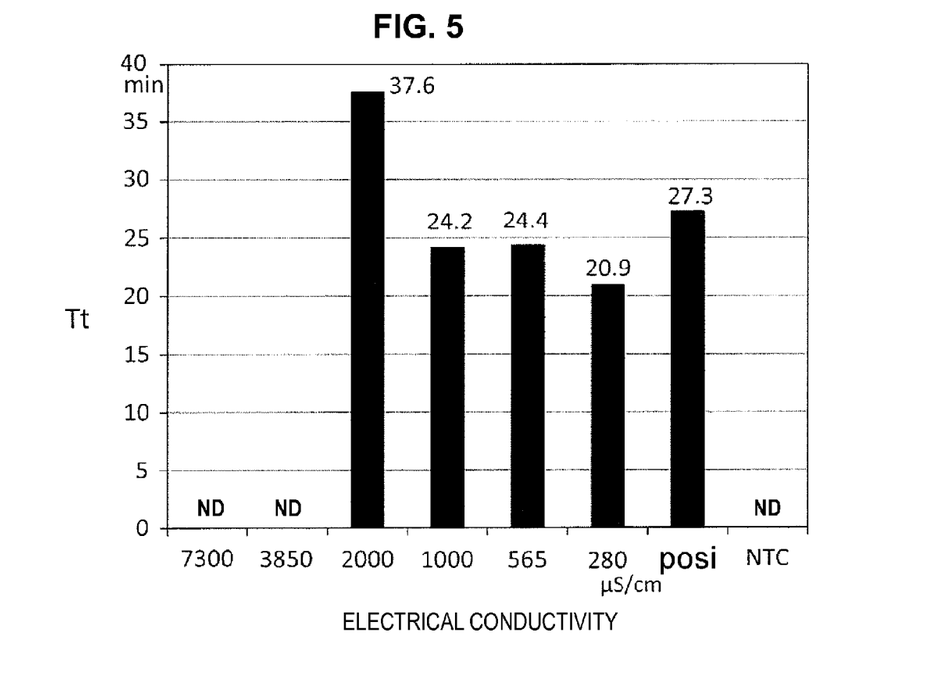
FIG. 5 is a graph illustrating a relationship between the electrical conductivity of a sample and the time required for a nucleic acid amplification reaction (Example 2).

The results of this example are shown in FIG. 5. The vertical axis in FIG. 5 represents the Tt value. The "posi" (positive control) shown in FIG. 5 is a test sample that did not contain normal saline solution, which was diluted with sterilized water so that the bifidobacteria genome concentration was 100 copies/µl. Further, "NTC" indicates a test sample that does not contain a template nucleic acid (bifidobacteria genome).

Nucleic acid amplification was not recognized for test samples having an electrical conductivity of 3,850 µS/cm or more (in FIG. 5, ND indicates that an amplified nucleic acid strand was not detected). On the other hand, nucleic acid amplification was recognized for test samples having an electrical conductivity of 2,000 µS/cm or less. Especially, the Tt value (20.9 to 24.4) of test samples having an electrical conductivity of 1,000 µS/cm or less was less than the posi Tt value (27.3), thereby confirming that the nucleic acids were amplified at about the same efficiency as the test sample not containing substances that inhibit the nucleic acid amplification reaction.

Example 3

3. Investigation of the Heating Temperature of the Sample that Enables Nucleic Acid Amplification The heating temperature for reducing the effects of inhibitory substances were investigated by focusing on the effects of the heating treatment performed on the substances included in the sample that inhibit the nucleic acid amplification reaction. In this example, as a pseudo-analyte, bovine plasma solutions containing EDTA were used. The bovine plasma solutions that was used had been desalted in advance by electrodialysis until the electrical conductivity reached 1,000 µS/cm or less.

The above-described bovine plasma solutions were dispensed into a vessel, heated for 10 minutes at a temperature of either 40° C., 50° C., 60° C., or 65° C., and then left at room temperature to cool. It is noted that in a preliminary investigation of this example, when bovine plasma was heated at 70° C. or more, it was confirmed that the bovine plasma turned into a gel, and was not suitable as a sample for a nucleic acid amplification reaction.

Sterilized water was added to the heated bovine plasma solutions, and the resultant solutions were diluted by a dilution factor of any of 1 (not diluted), 3 or 5. A bifidobacteria genome that had been separately purified was admixed into each of the diluted plasma solutions to a concentration of 100 copies/µl. Non-heated bovine plasma solutions were similarly diluted with sterilized water by a factor of 1 (not diluted), 3 or 5, and then a bifidobacteria genome was added to a concentration of 100 copies/µl. These heated or non-heated bovine plasma-containing test samples were charged with an equal amount of LAMP reagent, and the nucleic acids in the test samples were then amplified based on the LAMP method.

Figure 6:
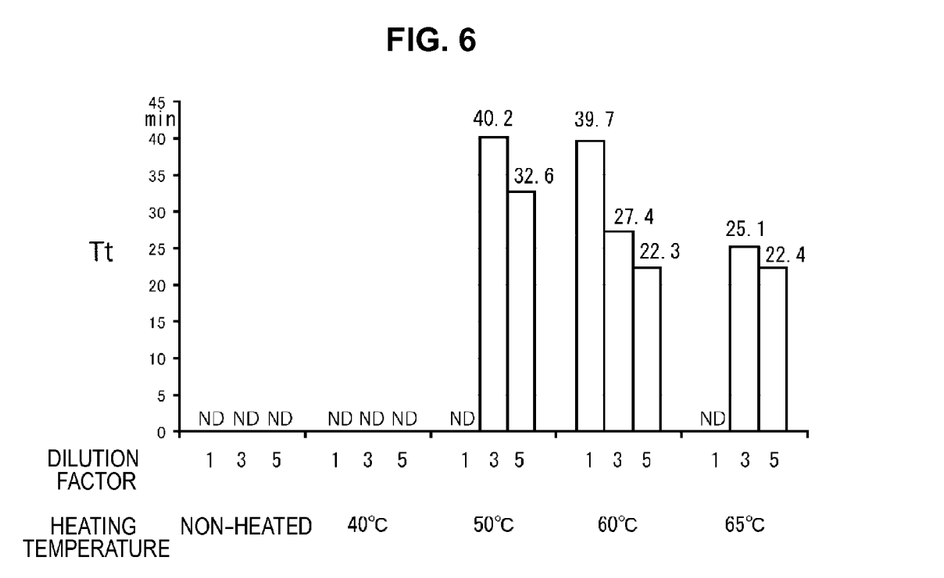
FIG. 6 is a graph illustrating a relationship between the heating temperature of a sample and the time required for a nucleic acid amplification reaction (Example 3).

The results of this example are shown in FIG. 6. The vertical axis in FIG. 6 represents the Tt value. As shown in FIG. 6, for the test sample containing non-heated bovine plasma solution, nucleic acid amplification was not recognized (in FIG. 6, ND indicates that an amplified nucleic acid strand was not detected). Further, for the test sample having a heating temperature of 40° C., nucleic acid amplification was not recognized. On the other hand, for the test samples having a heating temperature of 50° C. or 65° C., although nucleic acid amplification was not recognized for the test sample that was not diluted with sterilized water (in FIG. 6, dilution factor 1), nucleic acid amplification was recognized for the test samples having a dilution factor of 3 and 5. For the test samples having a heating temperature of 60° C., nucleic acid was recognized regardless of whether or not dilution was performed with sterilized water.

Based on the results of this example, it was confirmed that the effects of components included in the plasma that inhibit a nucleic acid amplification reaction can be reduced by heating the sample, showing that heating of the sample is effective in preparing a sample for a nucleic acid amplification reaction. As the heating temperature, for example, 50° C. or more to 65° C. or less is preferred.

Further, for the test samples that were treated under the same heating conditions, the test samples that were diluted more exhibited a lower Tt value and a more effective nucleic acid amplification reaction. This result shows that the effects of the substances included in the sample that inhibit the nucleic acid amplification reaction can be reduced by diluting the sample.

Example 4

4. Investigation of the Sample Heating Time that Enables Amplification of the Nucleic Acids Contained in the Sample In Example 3 it was shown that heating the sample is an effective method to prepare a sample for a nucleic acid amplification reaction. Accordingly, in this example, an investigation was carried out into the heating time of the sample.

Figure 7:
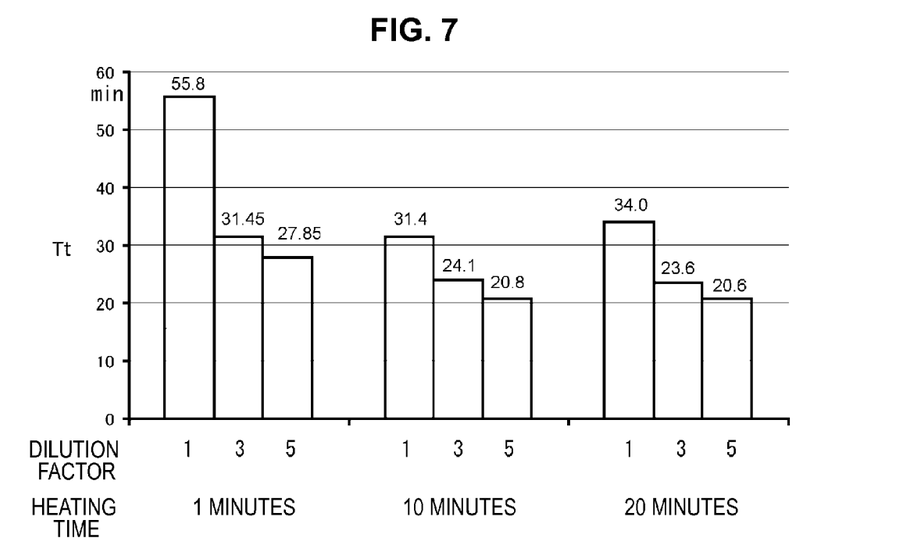
FIG. 7 is a graph illustrating a relationship between the heating time of a sample and the time required for a nucleic acid amplification reaction (Example 4).

In this example, similar to Example 3, bovine plasma desalted by electrodialysis so as to have an electrical conductivity of 1,000 µS/cm or less was used for a pseudo-analyte. The bovine plasma was dispensed into vessels, and heated at 60° C. for any of 1 minute, 10 minutes, or 20 minutes. The heated bovine plasma solutions were left on ice to cool. Then, the bovine plasma solutions were charged with sterilized water so as to have a dilution factor of any of 1 (not diluted), 3, or 5. A bifidobacteria genome (100 copies/µl) was added to these bovine plasma solutions. A LAMP reagent in an equal amount to the bovine plasma solutions was added, and nucleic acid amplification was carried out based on the LAMP method. The results of this example are shown in FIG. 7. The vertical axis in FIG. 7 represents the Tt value. As shown in FIG. 7, for the test sample heated at 60° C., nucleic acid amplification was confirmed for each of the heating times of 1 minute, 10 minutes, and 20 minutes. However, compared with the test sample having a heating time of 1 minute, the 10 minute test sample had a smaller Tt value. This shows that a heating time of 10 minutes provides a more efficient nucleic acid amplification reaction. No great difference in Tt values was seen between the test samples having a heating time of 10 minutes and 20 minutes. Based on the results of this example, it was shown that a sample heating time of even 1 minute is effective in the preparation of a sample for a nucleic acid amplification reaction. Further, it was also shown that a sample heating time of 10 minutes or more is preferred, because the nucleic acid amplification reaction is more efficient.

Example 5

5. Investigation of the Cooling Method of the Heated Sample

The above-described Examples 3 and 4 showed that heating the sample is an effective method to prepare a sample for a nucleic acid amplification reaction. Accordingly, in this example, an investigation was carried out on the effects on a nucleic acid amplification reaction of differences in the cooling method of a heated sample.

In this example, similar to Examples 3 and 4, bovine plasma desalted by electrodialysis so as to have an electrical conductivity of 1,000 µS/cm or less was used for a pseudo-analyte. The bovine plasma was dispensed into vessels, and heated at 60° C. for 10 minutes. The heated bovine plasma solutions were cooled by either a gradual cooling method or a rapid cooling method. In "gradual cooling", the vessel containing the heated bovine plasma was left at room temperature to cool. In "rapid cooling", the vessel containing the heated bovine plasma was left on ice to cool. Then, the bovine plasma solutions that had been cooled by "gradual cooling" or "rapid cooling" were charged with sterilized water so as to have a dilution factor of any of 1 (not diluted), 3, or 5. A bifidobacteria genome that had been purified in advance was added to a concentration of 100 copies/µl. A LAMP reagent in an equal amount to the bovine plasma solutions was added to the test samples containing these bovine plasma solutions, and nucleic acid amplification was carried out based on the LAMP method.

Figure 8:
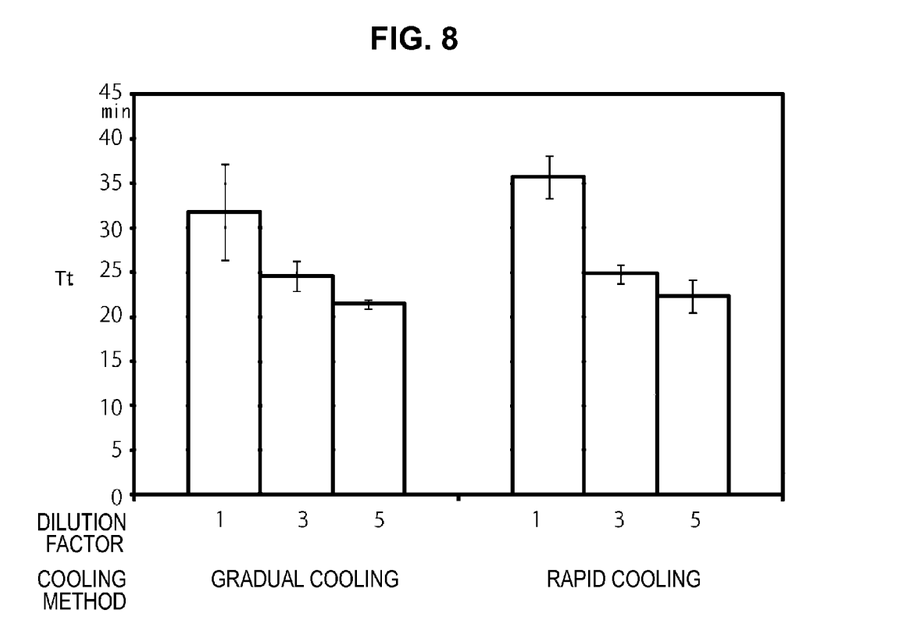
FIG. 8 is a graph illustrating a relationship between a cooling method after sample heating and the time required for a nucleic acid amplification reaction (Example 5).

The results of this example are shown in FIG. 8. The vertical axis in FIG. 8 represents the Tt value. As shown in FIG. 8, no great difference in Tt values was found between the "gradual cooling" and "rapid cooling" cooling methods. Thus, an effect on the nucleic acid amplification reaction based on differences in the cooling method of the sample was not recognized.

Example 6

6. Investigation of the Release of Nucleic Acids in the Cells from the Cells by Ultrasonic Treatment of the Sample An investigation was carried out whether or not nucleic acids in the cells included in the sample are released from the cells by irradiating ultrasonic waves. A test sample was produced by collecting cultured bifidobacteria, and preparing a bifidobacteria dispersion having 1,000 bifidobacteria bacteria per µl in sterilized water using a blood cell counter. The test sample was dispensed into vessels, and one test sample was irradiated for 60 seconds with 38 kHz ultrasonic waves using a horn immersion type ultrasonic wave generation device. Further, another test sample was irradiated for 10 minutes with 2.4 MHz ultrasonic waves using a non-contact type ultrasonic wave generation device. Supernatant was collected from each of the test samples that had been subjected to ultrasonic wave irradiation. Supernatant was similarly collected from a bifidobacteria dispersion that had not been irradiated with ultrasonic waves.

The supernatant of each of the test samples that had been subjected to the ultrasonic treatment and the supernatant of a non-treated test sample were subjected to real time PCR, and the number of genome copies was quantified. To calculate the number of genome copies, a dilution series of sterilized water containing purified bifidobacteria genome in a predetermined concentration was produced, and real time PCR was carried out on each dilution series to produce a calibration curve.

Figure 9:
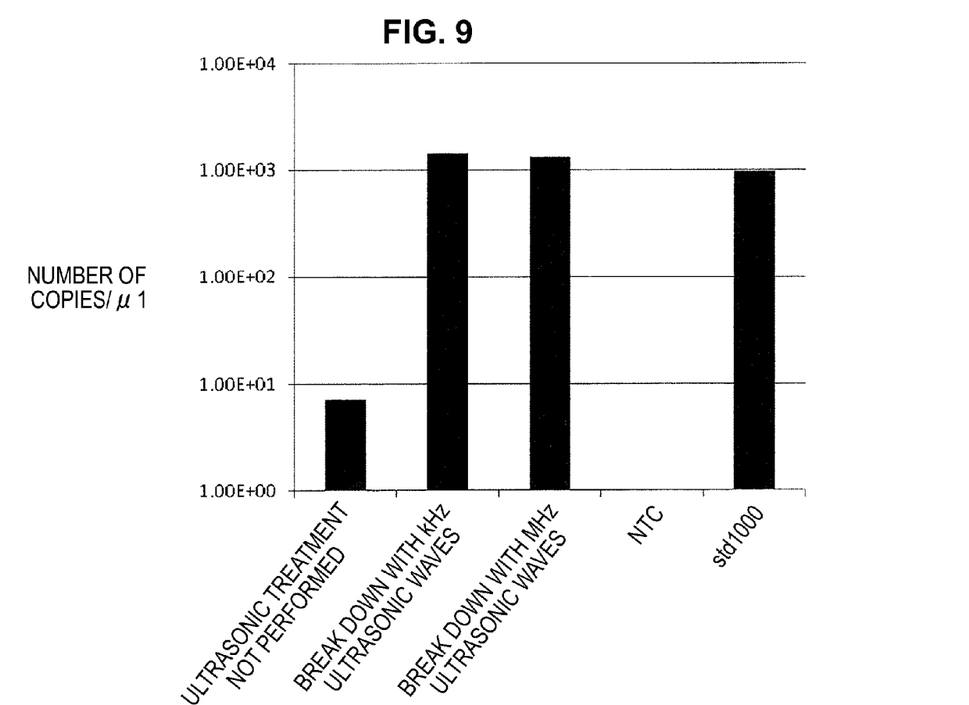
FIG. 9 is a graph illustrating release of a nucleic acid from a cell in a sample by ultrasonic treatment (Example 6).

The results of this example are shown in FIG. 9. The vertical axis in FIG. 9 represents the concentration (number of copies/µl) of the bifidobacteria genome. Further, "NTC" indicates a test sample that does not contain nucleic acid, and "std 1000" indicates a test sample containing purified bifidobacteria genome in a concentration of 1,000 copies/µl.

The results of this example are shown in FIG. 9. The vertical axis in FIG. 9 represents the concentration (number of copies/µl) of the bifidobacteria genome. Further, "NTC" indicates a test sample that does not contain nucleic acid, and "std 1000" indicates a test sample containing purified bifidobacteria genome in a concentration of 1,000 copies/µl.

As shown in FIG. 9, even for the ultrasonic waves at the kHz level that were used by the horn immersion type ultrasonic wave generation device (refer to FIG. 9, kHz ultrasonic wave breakdown), and even for the ultrasonic waves at the MHz level that were used by the non-contact type ultrasonic wave generation device (refer to FIG. 9, MHz ultrasonic wave breakdown), it was confirmed that the bifidobacteria cells were broken down by the ultrasonic waves, and that about the same level of bifidobacteria genome as the "std 1000", which contains purified bifidobacteria genome, was released into the sterilized water. Based on these results, it was confirmed that the ultrasonic treatment of the sample was an effective treatment to increase the efficiency of a nucleic acid amplification reaction when the nucleic acids present in the cells contained in the sample are the amplification target.

Example 7

7. Preparation of Sample for a Nucleic Acid Amplification Reaction Using Sample Preparation Vessel According to the Present Technology An investigation whether or not a sample for a nucleic acid amplification reaction could be prepared using the above-described preparation vessel A (refer to FIG. 2) was carried out.

In this example, pig spinal fluid to which bifidobacteria had been added was used for the sample. Tap water serving as an electrolyte was filled in the electrolyte-containing sections 12 and 13. Further, a negative ion-exchange membrane (average pore size 100 nm) was used for the porous membrane 31 separating the sample containing-section 11 and the electrolyte-containing section 12, and a positive ion-exchange membrane (average pore size 100 nm) was used for the porous membrane 31 separating the sample containing-section 11 and the electrolyte-containing section 13.

The bifidobacteria-containing pig spinal fluid serving as the sample was filled into the sample containing-section 11 illustrated in FIG. 11, and the whole preparation vessel A was heated for 10 minutes at 60° C. After the heating, the preparation vessel A was left at room temperature to cool. Then, a voltage was applied to the anode 22 and the cathode 23 to perform electrodialysis on the sample contained in the sample containing-section 11. This was continued until the electrical conductivity reached 1,000 µS/cm. An ultrasonic treatment was then carried out on the sample that had been subjected to electrodialysis by transmitting ultrasonic waves (2.4 MHz) generated by the ultrasonic wave generation device via the ultrasonic wave transmission portion 14 to the sample.

After the ultrasonic treatment had finished, the sample was collected from the preparation vessel A, and a part of the sample was dispensed into a vessel. A LAMP reagent in an equal amount to the dispensed sample was admixed into the vessel containing the sample, and the resultant mixture was subjected to a LAMP reaction. A Q probe was used to detect the amplified nucleic acid strands based on an AMP method. Fluorescently-labeled cytosine is present at the tip of a Q probe. When the Q probe is not hybridized with a nucleic acid strand, a fluorescent substance emits light. On the other hand, when the Q probe is hybridized with a nucleic acid strand, since the fluorescently-labeled cytosine pairs with guanine, the fluorescent substance does not emit light. Therefore, when a target nucleic acid strand of the Q probe that is capable of hybridizing in a complementary manner with the Q probe is present in the test sample, during annealing, the Q probe does not emit light. Further, as the amplification of the target nucleic acid strand of the Q probe by the nucleic acid amplification reaction proceeds, the amount of light emitted by the Q probe decreases.

Figure 10:
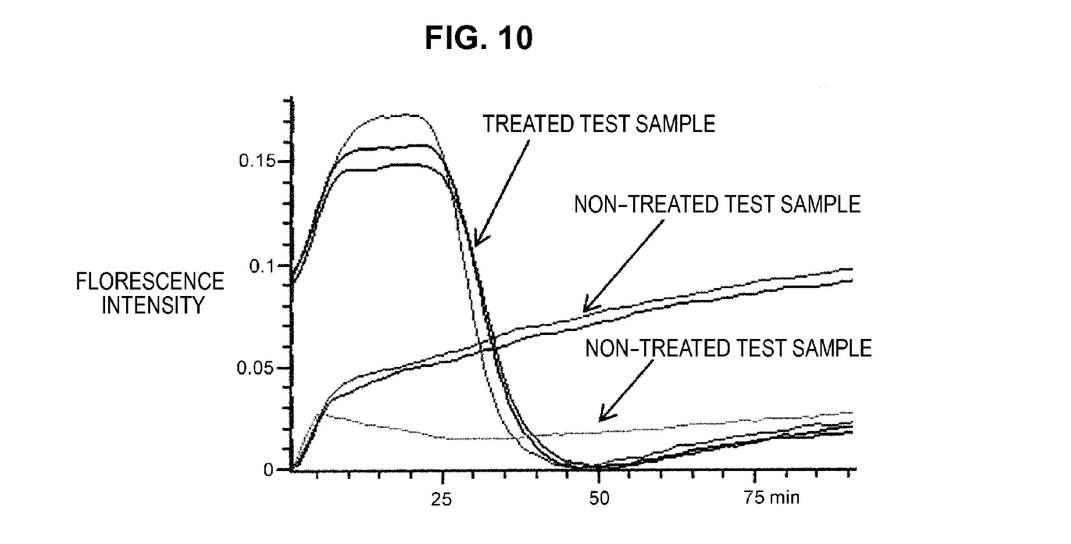
FIG. 10 is a graph illustrating the results of a nucleic acid amplification reaction of a sample containing a bacterial genome prepared by the method for preparing a sample for a nucleic acid amplification reaction according to the present technology (Example 7).

The results of this example are shown in FIG. 10. The vertical axis in FIG. 10 represents the fluorescence intensity of the test sample, and the horizontal axis represents the time (minutes) since the LAMP reaction started. For a sample prepared using the above-described preparation vessel A (treatment test sample), the fluorescence intensity started to decrease about 25 minutes after the LAMP reaction started. At the 50 minute mark, the fluorescence intensity had decreased by 90% or more compared with the 20 minute mark. Based on this result, amplification of the nucleic acids contained in the treated test sample was confirmed (refer to FIG. 10, treated test sample). On the other hand, for a test sample not prepared using the above-described preparation vessel A (non-treated test sample), the large decrease in the fluorescence intensity seen for the treated test sample was not observed, so that nucleic acid amplification was not confirmed (refer to FIG. 10, non-treatment sample). Based on the results of this example, it was shown that by preparing a sample as a sample for a nucleic acid amplification reaction using the preparation vessel A according to the present technology, a state suitable to a nucleic acid amplification reaction could be achieved.

According to the method for preparing a sample for a nucleic acid amplification reaction according to the present technology, a sample suitable to a nucleic acid amplification reaction can be prepared by a simple operation. Consequently, the method for preparing a sample for a nucleic acid amplification reaction according to the present technology can be used as a method for preparing samples to be used in nucleic acid testing for clinical genotyping and pathogen identification.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

A preparation vessel
B preparation vessel
1 body
11 sample containing-section
12 electrolyte-containing section
13 electrolyte-containing section
14 ultrasonic wave transmission portion
22 anode
23 cathode
31 porous membrane
4 power supply
5 heating unit
6 ultrasonic wave generation unit

The invention claimed is:

1. A method of preparing a sample for nucleic acid amplification reaction, the method comprising:
    applying heat to a nucleic acid-containing sample such that a heating temperature of the sample is 50° C. or more; and
    bringing an electrical conductivity of the sample to 2,000 µS/cm or less.

2. The method for preparing the sample for the nucleic acid amplification reaction according to claim 1, wherein a porous membrane is used in bringing the electrical conductivity of the sample to 2,000 µS/cm or less, wherein the porous membrane has an average pore size of 100 nm or less.

3. The method for preparing the sample for the nucleic acid amplification reaction according to claim 1, wherein the heating temperature of the sample is 50° C. or more to 65° C. or less.

4. The method for preparing the sample for the nucleic acid amplification reaction according to claim 3, the method further comprising:
performing an ultrasonic treatment on the sample.

5. The method for preparing the sample for the nucleic acid amplification reaction according to claim 1, the method further comprising:
diluting the sample.

6. The method for preparing the sample for the nucleic acid amplification reaction according to claim 1, wherein the sample includes a sample derived from a living organism.

7. The method for preparing the sample for the nucleic acid amplification reaction according to claim 6, wherein the sample derived from the living organism is one of plasma, serum, or cerebrospinal fluid.

8. The method for preparing the sample for the nucleic acid amplification reaction according to claim 7, wherein the sample derived from the living organism is cerebrospinal fluid.

9. The method for preparing the sample for the nucleic acid amplification reaction according to claim 7, further comprising:
performing an ultrasonic treatment on the sample if the nucleic acid is present in a cell included in the sample derived from the living organism.

10. The method for preparing the sample for the nucleic acid amplification reaction according to claim 7, wherein when the sample derived from the living organism is one of the plasma or the serum, the method comprises:
bringing the electrical conductivity of the sample to 2,000 µS/cm or less;
applying heat to the sample such that the heating temperature of the sample is 50° C. or more; and
diluting the sample after the application of heat to the sample such that the heating temperature of the sample is 50° C. or more.

11. The method for preparing the sample for the nucleic acid amplification reaction according to claim 1, wherein the method for preparing the sample is an isothermal nucleic acid amplification method.

12. The method for preparing the sample for the nucleic acid amplification reaction according to claim 11, wherein the isothermal nucleic acid amplification method for preparing the sample is performed based on a loop-mediated isothermal amplification method.

13. The method for preparing the sample for the nucleic acid amplification reaction according to claim 1, wherein the applying of the heat to the nucleic acid-containing sample is performed for 10 minutes or more.

14. The method for preparing the sample for the nucleic acid amplification reaction according to claim 1, further comprising bringing the electrical conductivity of the sample to 1,000 µS/cm or less.

\* \* \* \* \*